(12) United States Patent
Laurent

(10) Patent No.: US 6,538,039 B2
(45) Date of Patent: *Mar. 25, 2003

(54) PHARMACEUTICAL DOSAGE FORM FOR TRANSDERMAL ADMINISTRATION

(75) Inventor: Philippe Laurent, Oullins (FR)

(73) Assignee: Laboratoire L. Lafon, Maisons Alfort (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/741,967

(22) Filed: Oct. 31, 1996

(65) Prior Publication Data

US 2002/0111387 A1 Aug. 15, 2002

Related U.S. Application Data

(63) Continuation-in-part of application No. 08/428,958, filed on Apr. 26, 1995, now abandoned.

(30) Foreign Application Priority Data

Apr. 29, 1994 (FR) .............................. 94 05272

(51) Int. Cl.⁷ ..................... A61K 47/30; A61K 7/021; A61K 7/44; A61K 6/00
(52) U.S. Cl. ................. 514/772.2; 424/60; 424/63; 424/401
(58) Field of Search .................. 514/772.2; 424/60, 424/401, 63

(56) References Cited

U.S. PATENT DOCUMENTS

| 3,836,647 A | | 9/1974 | Lange | |
| 5,185,150 A | * | 2/1993 | De Luca et al. | 424/195.1 |
| 5,330,747 A | * | 7/1994 | Krzysik | 424/63 |
| 6,211,425 B1 | * | 4/2001 | Takayasu et al. | 602/41 |

FOREIGN PATENT DOCUMENTS

| DE | 2140491 | | 2/1973 | |
| EP | 0164999 | | 12/1985 | |
| EP | 0177920 | * | 4/1986 | |
| EP | 0289900 | | 11/1988 | |
| EP | 0409550 | | 1/1991 | |
| EP | 0512814 | * | 11/1992 | |
| EP | 0521455 | | 1/1993 | |
| EP | 0560014 | | 9/1993 | |
| WO | 8503434 | * | 8/1985 | 424/449 |

OTHER PUBLICATIONS

French Search Report.

* cited by examiner

Primary Examiner—Thurman K. Page
Assistant Examiner—S. Tran
(74) Attorney, Agent, or Firm—Jacobson Holman PLLC

(57) ABSTRACT

The present invention relates to a process for administering an active principle to a patient transdermally, which comprises the formation of a film on the patient's skin, by applying to the skin a liquid solution which consists essentially of:

a) a lipophilic active principle,
b) from 2.5 to 25% by weight of a silicone-based adhesive polymer composition,
c) from 0 to 25% by weight of an absorption promoter, and
d) from 25 to 95% by weight of volatile solvents comprising volatile silicones.

13 Claims, No Drawings

PHARMACEUTICAL DOSAGE FORM FOR TRANSDERMAL ADMINISTRATION

The present application is a continuation-in-part of U.S. patent application Ser. No. 08/428,958, filed Apr. 26, 1995, now abandoned, the disclosure of which is incorporated herein by reference.

The present invention relates to a new pharmaceutical dosage form for the transdermal administration of an active principle.

The 1980s saw the development of transdermal systems which are applied to a delimited area of the skin and which serve as a carrier or vehicle for one or more active principles, which are generally intended to exert a systemic action after release and passage through the cutaneous barrier.

These systems, generally referred to as "transdermal patches", afford a number of advantages over the traditional dermatological forms such as ointments, salves, gels, solutions and lotions, namely:

direct and continuous entry into the general circulation,
elimination of the hepatic first-pass effect and/or of degradation in the digestive tract, with a consequent decrease in side effects,
extended duration of action,
maintenance of a constant level of active principles in the plasma,
increase in patient compliance through decrease in the frequency of dosage,
decrease in inter-individual variations,
control over the dose administered as a result of a matrix or membrane system with a reservoir,
production of a constant concentration of active principle during the period of the application.

Despite the degree of innovation provided by these systems, only a very small number of specialities exist today in this form. This is due to the fact that these devices demand:

a very sophisticated technology of manufacture,
few production sites which belong to a few large groups who have a monopoly of them,
this leads to a high cost of manufacture and to a substantial cost and sale price. These systems are, in actual fact, reserved for expensive products.

The present invention is directed towards providing new pharmaceutical dosage forms for the transdermal administration of an active principle which are very simple to use, and do not require massive, complex and costly industrial plants,
which are multi-purpose; both from the standpoint of formulation and as regards the procedures for application when used,
which are advantageous from an economic standpoint with a lower production cost.

To this end, the subject of the present invention is a composition intended to form a film on the skin for the transdermal administration of an active principle, which comprises as liquid solution:

a) a lipophilic active principle
b) from 2.5 to 60% in weight, and advantagesouly from 2.5 to 25% by weight, of a silicone-based adhesive polymer composition
c) from 0 to 25% by weight, of an absorption promoter, and
d) from 25 to 95% by weight, and advantageously from 50 to 95% by weight, of volatile solvents comprising volatile silicones.

The subject of the present invention is also:

the use of a composition which comprises:
a) an active principle
b) from 2.5 to 60% by weight, and advantageously from 2.5 to 25% by weight, of a silicone) based adhesive polymer composition
c) from 0 to 25% by weight of an absorption promoter, and
d) from 25 to 95% by weight, and advantageously from 50 to 95% by weight, of volatile solvents comprising volatile silicones for the production of a film on a patient's skin for the transdermal administration of the active principle;

a process for administering an active principle to a patient transdermally, which comprises the formation of a film on this patient's skin by applying to the skin a liquid solution which comprises:
a) an active principle
b) from 2.5 to 60% by weight and advantageously from 2.5 to 25% by weight of a silicone-based adhesive polymer composition
c) from 0 to 25% by weight of an absorption promoter, and
d) from 25 to 95% by weight, and advantageously from 50 to 95% by weight, of volatile solvents comprising volatile silicones.

In the present invention, active principle denotes chiefly a medicinal product or substance having therapeutic properties.

These medicinal products are, in particular, lipophilic vitamins such as vitamins D and E and their derivatives, hormones such as calcitonin, steroids such as oestradiol and its esters, a progestogen (such as norethisterone) and prednisone, or nicotine.

The percentages of the active principles in the compositions of the invention clearly depend on the nature of the active principle. Generally, the percentages are from 0.01 to 10% by weight.

According to the invention, silicone-based polymer composition is understood to mean a composition containing silicone-based polymers or silicone-based copolymers.

These silicones, which will be designated according to the nomenclature of the CTFA (Cosmetic, Toiletry and Fragrance Association) Dictionary, comprise, in particular, polydimethylsiloxane oils or polydimethylsiloxane oils modified with ionic or nonionic organic groups.

As an example of polydimethylsiloxane oils, there may be mentioned dimethicones of formula:

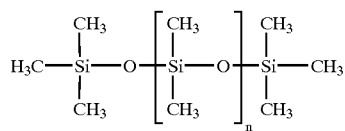

where n is an integer below 5,000, and dimethiconols, which are dimethyl silicones terminated with hydroxyl groups.

As an example of modified polydimethylsiloxanes, there may be mentioned dimethicone copolyols, which are polymers of dimethylsiloxane containing polyoxyethylene and/or polyoxypropylene side chains.

The silicone-based adhesive polymer composition preferably represents 2.5 to 12% and more advantageously from 2.5 to 10% of the weight of the composition, The absorption promoters may be selected in particular, from propylene glycol, hexylene glycol, propylene glycol dipelargonate, glyceryl monoethyl ether, diethylene glycol, monoglycerides, monooleate of ethoxylated glycerides (with 8 to 10 ethylene oxide units), Azone (1-dodecylazacycloheptan-2-one), 2-(n-nonyl)-1,3-dioxolane, isopropylmyristate, octylmyristate, dodecylmyristate, myristyl alcohol, lauryl alcohol, lauric acid, lauryl lactate, terpinol, 1-menthol, d-limonene, β-cyclodextrin and its derivatives or surfactants such as polysorbates, sorbitan esters, sucrose esters, fatty acids, bile salts, or alternatively lipophilic and/or hydrophilic and/or amphiphilic products such as poly-glycerol esters, N-methylpyrrolidone, polyglycosylated glycerides and cetyl lactate.

The absorption promoter preferably represents from 5 to 25% of the weight of the composition.

As volatile silicone, it is possible to use polydimethylcyclosiloxanes, that is to say compounds of formula:

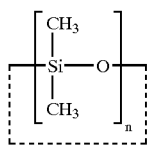

where n is between 3 and 6 on average, and in particular compounds in which n=4 or 5, as well as linear polysiloxanes such as hexamethyldisiloxane or dimethicones of low molecular mass.

In addition to the volatile silicones it is also possible to use other solvents such as ethanol, isopropanol, chloroform, heptane, ethyl acetate, preferably in an amount representing up to 25% by weight, and more preferably up to 20% by weight of the compositions. Water should be avoided since water is not compatible with the polysiloxanes.

The composition according to the invention may be contained in a dispensing apparatus which delivers defined and reproducible doses of composition. For example, the dispensing apparatus delivers a drop of composition, and this drop may be spread on the skin using a brush or using a ball which is rolled over the skin.

The present invention finds an especially advantageous use for the transdermal administration of vitamin $D_3$ (cholecalciferol).

Recent studies tend to show that all the populations of Western countries, and especially European countries, are lacking in Vitamin D in winter. The phenomenon is of less significance in the United States and in the Scandinavian countries which have a vitamin $D_3$-enriched diet.

In general, hypovitaminosis has been observed in the elderly individuals of all countries, and manifests itself in an osteomalacia and abnormal phenomena in bone chemistry.

The causes of deficiency are:
quantitatively and qualitatively insufficient dietary intake: eggs, butter, liver, fatty fish, etc.
lack of sunshine, since cutaneous synthesis takes place under the effect of UV rays. This source of supply of natural vitamin D is strongly dependent on climatic conditions.
malabsorption syndrome: in elderly subjects, there is a decrease in the intestinal absorption of vitamin D as a result of the decrease in liver and kidney functions.

At the present time, the specialities available on the market are essentially presented in pharmaceutical dosage forms for the oral route and a few for administration by injection (IM). Now, the oral route is not always well assimilated, and administration by injection is not always accepted by elderly individuals.

The subject of the present invention is hence, more specifically, a liquid solution intended to form a film on the skin for the transdermal administration of vitamin $D_3$ or a hydroxylated derivative of vitamin $D_3$, and which comprises:
a) vitamin $D_3$ or a hydroxylated derivative of vitamin $D_3$
b) from 5 to 60% by weight, and preferably from 9 to 12% by weight, of a silicone-based adhesive polymer composition
c) from 0 to 25% by weight of an absorption promoter, and
d) from 25 to 95% by weight and preferably from 65 to 85% by weight, of a volatile solvent comprising a volatile silicone.

The present invention relates also to a liquid solution intended to form a film on the skin for the transdermal administration of an active ingredient selected from oestrogens, progestogens and mixtures thereof, and which comprises:
a) an active ingredient selected from oestrogens, progestogens and mixtures thereof,
b) from 2.5 to 25% by weight of a silicone based adhesive polymer composition
c) from 0 to 25% by weight of an absorption promoter
d) from 35 to 55% by weight of a volatile silicone, and
e) from 0 to 35% by weight of a volatile polar solvent.

The polar solvent is in particular selected from ethanol, ethyl acetate and mixtures thereof and the composition contains advantageously 0 to 20% by weight of ethanol and 0 to 15% by weight of ethyl acetate.

Examples of compositions according ot the invention will be given below.

EXAMPLES 1 TO 11

Compositions Based on Vitamin $D_3$

The compositions appearing in the table below were prepared by mixing the different constituents until a homogeneous solution was obtained.

|  | 1 (g) | 2 (g) | 3 (g) | 4 (g) | 5 (g) | 6 (g) | 7 (g) | 8 (g) | 9 (g) | 10 (g) | 11 (g) |
|---|---|---|---|---|---|---|---|---|---|---|---|
| Cholecalciferol | 0.0825 | 0.0825 | 0.600 | 1.050 | 0.750 | 0.300 | 0.0825 | 0.600 | 0.140 | 0.280 | 1.120 |
| Propylene glycol dipelargonate | — | — | 7.500 | 7.500 | 7.500 | 7.500 | — | 7.500 | 22.500 | 22.500 | 22.500 |
| Cyclomethicone/ | 30.000 | 30.000 | 22.500 | 22.500 | — | — | 30.000 | 22.500 | 76.658 | 75.818 | 70.778 |

-continued

| | 1 (g) | 2 (g) | 3 (g) | 4 (g) | 5 (g) | 6 (g) | 7 (g) | 8 (g) | 9 (g) | 10 (g) | 11 (g) |
|---|---|---|---|---|---|---|---|---|---|---|---|
| dimethiconol (1) | | | | | | | | | | | |
| Dimethicone/ dimethiconol (2) | — | — | — | — | 22.500 | 22.500 | — | — | — | — | — |
| Alpha-tocopherol (preservative) | — | 0.413 | — | 3.500 | — | 1.500 | — | — | 0.700 | 1.400 | 5.600 |
| BHT/benzalkonium chloride (3) (preservative) | — | — | — | — | — | — | BHT 0.495 | BHT 3.600 | (3) 0.002 | (3) 0.002 | (3) 0.002 |

(1) 13% Solution of dimethiconol in a cyclomethicone
(2) 13% Solution of dimethiconol in a dimethicone of low viscosity At the time of use, using an applicator system, a drop of the composition is deposited on the skin and is spread over a specified area.

The transdermal film forms after evaporation of the silicone solvent.

EXAMPLE 12

Composition Based on 1,2,5-dihydroxycholecalciferol

| A. | 1,25 -Dihydroxycholecalciferol | 2 µg |
|---|---|---|
| B. | Diethylene glycol monoethyl ether | 2.50% |
| C. | Glyceryl monooleate | 1.25% |
| D. | Propylene glycol dipelargonate | 1.25% |
| E. | Dimethylpolysiloxane in cyclomethicone (13% solution) | 55.00% |
| F. | Cyclomethicone | QS 100 µl |

EXAMPLE 13

Composition Based on Calcitonin

| A. | Calcitonin | 100 IU |
|---|---|---|
| B. | Azone | 10% |
| C. | Copolymer of polyacrylamide isoparaffin and polyoxyethylenated lauryl alcohols | 5% |
| D. | Propylene glycol | 20% |
| E. | Dimethicone and dimethiconol in cyclomethicone (13% solution) | 20% |
| F. | Polydimethylcyclosiloxane | QS 50 microliters |

EXAMPLE 14

Composition Based on Oestradiol Ester

| A. | Oestradiol propionic and nicotinic ester | 1.3 mg |
|---|---|---|
| B. | Diethylene glycol monoethyl ether | 5% |
| C. | Glyceryl monooleate | 2.5% |
| D. | Propylene glycol dipelargonate | 2.5% |
| E. | Dimethicone and dimethiconol in cyclomethicone (13% solution) | 55% |
| F. | Polydimethylcyclosiloxane | QS 100 µl |

EXAMPLE 15

Composition Based on Prednisone

| A. | Prednisone | 2 mg |
|---|---|---|
| B. | Azone | 5% |
| C. | Beta-cyclodextrin | 10% |
| D. | Dimethiconol in cyclomethicone (13% solution) | 20% |
| E. | Ethanol | 10% |
| F. | Polydimethylcyclosiloxane | QS 100 µl |

EXAMPLE 16

Composition Based on Calcitonin

| A. | Calcitonin | 100 IU |
|---|---|---|
| B. | Azone | 10% |
| C. | Copolymer of polyacrylamide isoparaffin and polyoxyethylenated lauryl alcohols | 5% |
| D. | Propylene glycol | 5% |
| E. | Dimethiconol in cyclomethicone (13% solution) | 40% |
| F. | Ethanol | 10% |
| G. | Polydimethylcyclosiloxane | QS 100 µl |

EXAMPLES 17 TO 22

The following compositions for the transdermal administration of 17β-oestradiol were prepared:

| Example | 17 | 18 | 19 | 20 | 21 | 22 |
|---|---|---|---|---|---|---|
| 17β-Oestradiol | 0.250 g | 0.250 g | 0.250 g | 0.250 g | 0.250 g | 0.250 g |
| PGDP(1) | 10.00 g | 10.00 g | 10.00 g | 20.00 g | 20.00 g | 20.00 g |
| SEPA(2) | | 2.00 g | 5.00 g | | 2.00 g | 5.00 g |

-continued

| Example | 17 | 18 | 19 | 20 | 21 | 22 |
|---|---|---|---|---|---|---|
| Ethanol | 20.00 g | 20.00 g | 20.00 g | 20.00 g | 20.00 g | 20.00 g |
| Silicone 1401[3] QS | 100.00 g | 100.00 g | 100.00 g | 100.00 g | 100.00 g | 100.00 g |

[1]Propylene glycol dipelargonate
[2]2-(n-Nonyl)-1,3-dioxolane
[3]13% solution of dimethiconol in a cyclomethicone.

A study of diffusion through human skin in vitro was performed with these compositions.

The method used is the following.

An exact amount of composition, measured volumetrically (10 μl) is applied to a human skin biopsy sliced with a dermatome (constant thickness 350 μm) and placed in a so-called Franz® static type diffusion cell. Contact is maintained for 2, 4, 6, 8, 10 and 24 hours. The samples of human skin originate from anatomical pieces taken from abdomen and/or breast during an operation for plastic surgery.

The survival fluid is a pH 7.4 phosphate buffer containing albumin (bovine serum albumin 15 g/l). At the end of each contact time, the fluid in the dermal compartment is sampled and the active principle it contains is assayed.

At the end of the 24 hours of contact, the skin surface is washed. The active principle remaining at the surface of the skin and carried into the washes is quantified.

| Example | 23 | 24 | 25 | 26 |
|---|---|---|---|---|
| Cholecalciferol | 0.534 g | 0.534 g | 0.534 g | 0.534 g |
| Alpha-tocopherol | 2.800 g | 2.800 g | 2.800 g | 2.800 g |
| PGDP[1] | 22.500 g | 22.500 g | 22.500 g | 22.500 g |
| SEPA ™[2] | 0.000 g | 2.000 g | 5.000 g | 10.000 g |
| Methyl para-hydroxybenzoate | 0.250 g | | | |
| Propyl para-hydroxybenzoate | 0.100 g | | | |
| Ethanol | 0.650 g | | | |
| Silicone[3] QS | 100,000 g | 100,000 g | 100,000 g | 100,000 g |

[1]Propylene glycol dipelargonate
[2]2-(n-Nonyl)-1,3-dioxolane
[3]13% Solution of dimethiconol in a cyclomethicone.

The procedure was the same as that used with the compositions of Examples 17 to 22, applying 10 mg of composition (53.40 μg of cholecalciferol).

The results are given in the table below:

| Amounts in μg of vitamin $D_3$ absorbed (± SD) | | 2 hours | 4 hours | 6 hours | 8 hours | 10 hours | 24 hours |
|---|---|---|---|---|---|---|---|
| Example 23: | (μg) | 1.0820 | 1.6223 | 2.1175 | 2.5170 | 2.8520 | 4.4525 |
| | (±) | 0.3667 | 0.4696 | 0.6116 | 0.7228 | 0.8417 | 1.1364 |
| Example 24: | (μg) | 1.1173 | 1.52220 | 1.8880 | 2.1758 | 2.4260 | 3.6465 |
| | (±) | 0.2789 | 0.3773 | 0.4594 | 0.5138 | 0.5549 | 0.6630 |
| Example 25: | (μg) | 1.3078 | 1.8285 | 2.3330 | 2.7273 | 3.0893 | 4.8973 |
| | (±) | 0.5660 | 0.7634 | 0.9587 | 1.1191 | 1.2645 | 1.8922 |
| Example 26: | (μg) | 1.1983 | 1.8933 | 2.4513 | 2.8553 | 3.2080 | 4.7830 |
| | (±) | 0.5044 | 0.4308 | 0.4390 | 0.4196 | 0.3928 | 0.3038 |

The results obtained after 24 hours are given in the following table, in % absorbed of the dose applied.

| Example | |
|---|---|
| 17 | 2.1 ± 1.0 |
| 18 | 2.7 ± 1.1 |
| 19 | 3.8 ± 0.9 |
| 20 | 4.4 ± 1.7 |
| 21 | 4.5 ± 2.5 |
| 22 | 9.4 ± 3.1 |

EXAMPLES 23 TO 26

The following compositions for the transdermal administration of cholecalciferol were prepared.

EXAMPLE 27

The following solution was prepared:

| | |
|---|---|
| Medroxyprogesterone acetate (MPA) | 0.50 g |
| Ethanol | 20.00 g |
| Ethyl acetate | 10.00 g |
| Propyleneglycol dipelargonate | 20.00 g |
| Silicone 1401 (13% solution of dimethiconol in a cyclomethicone) | 49.50 g |

This solution is used to form a progestogen transdermal film on the skin.

EXAMPLE 28

The following solution was prepared:

| | |
|---|---|
| Medroxyprogesterone acetate (MPA) | 1.00 g |
| 17β-oestradiol | 0.20 g |
| Estasan ® (1) | 5.00 g |
| Propyleneglycol dipelargonate | 20.00 g |
| Ethanol | 20.00 g |
| Ethyl acetate | 10.00 g |
| Silicone 1401 | 44.25 g. |

(1) Estasan ® is a trademark for glycerol esters of saturated fatty acids (fractionated coconut oil).

1 g of this film forming solution gives 2 mg of 17 β-oestradiol and 10 mg of MPA.

EXAMPLE 29

The following solution was prepared:

| | |
|---|---|
| 17β-oestradiol | 0.50 g |
| Norethisterone acetate (NETA) | 1.00 g |
| Estasan ® | 5.00 g |
| Propyleneglycol dipelargonate | 20.00 g |
| Ethanol | 20.00 g |
| Ethyl acetate | 10.00 g |
| Silicone 1401 | 43.50 g |

1 g of this solution gives 5 mg of 17 β-oestradiol and 10 mg of norethisterone acetate.

EXAMPLE 30

The following solution was prepared:

| | |
|---|---|
| 17β-oestradiol | 1.00 g |
| Norethisterone acetate | 0.50 g |
| SEPA (1) | 5.00 g |
| Propyleneglycol dipelargonate | 20.00 g |
| Ethanol | 20.00 g |
| Ethyl acetate | 10.00 g |
| Silicone 1401 | 43.50 g |

(1)2-(n-nonyl)-1,3-dioxolane.

1 g of this solution gives 10 mg of 17β-oestradiol and 5 mg of norethisterone acetate.

EXAMPLES 31 AND 32

Compositions Based on Vitamin $D_3$.
The following solutions were prepared.

| Example | 31 | 32 |
|---|---|---|
| Cholecalciferol | 0.534 g | 0.067 g |
| α-tocopherol | 2.800 g | 0.350 g |
| Propyleneglycol dipelargonate | 22.500 g | 22.500 g |
| Methylparahydroxybenzoate | 0.250 g | 0.250 g |
| Propylparahydroxybenzoate | 0.100 g | 0.100 g |
| Ethanol | 0.650 g | 0.650 g |
| Silicone 1401 | 73.700 g | 76.083 g |

A study of the efficiency of these solutions was performed.

Two groups of patients (15 patients for each group) to the skin of which were applied these compositions each day for 60 days by delivering 300 mg of cholecalciferol film forming solution (one drop from a delivery system), corresponding respectively to 6400 IU and 800 IU of vitamin $D_3$.

The increases (mean values) of 25-hydroxycholecalciferol between the day just before the treatment (baseline) and the day after 60 days of treatment, were 60% for the group receiving 6400 IU/day and 43% for the group receiving 800 IU/day as compared to baseline value. These results show clearly the true transcutaneous and systemic absorption of vitamin $D_3$, which is proportional to the dose delivered to the skin, by using the transdermal film forming solution.

EXAMPLES 33, 34 AND 35

Compositions for the Transdermal Administration of Oestradiol.

The following solutions were prepared.

| Examples | 33 | 34 | 35 |
|---|---|---|---|
| Oestradiol | 0.5 g | 0.5 g | 1.0 g |
| Ethyl acetate | | | 10.0 g |
| Ethanol | 20.0 g | 20.0 g | 20.0 g |
| Etasan ® | 5.0 g | — | 5.0 g |
| SEPA | — | 5.0 g | — |
| Propyleneglycol dipelargonate | 20.0 g | 20.0 g | 20.0 g |
| Silicone 1401 | 54.5 g | 54.5 g | 44.0 g |

An exact amount of each solution is applied to femal hairless rat skin, in vitro. With these solutions for a mean amount of 45 μg of oestradiol, about 30 μg of oestradiol are absorbed by the skin, i.e. passed in or through the skin in 24 hours.

What is claimed is:

1. Process for transdermally administering a lipophilic active ingredient, comprising applying to the skin of a patient a liquid solution to effect formation of a film on the patient's skin, wherein the liquid solution comprises:

a) a lipophilic active ingredient selected form the group consisting of hormones, steroids, and lipophilic vitamins, b) from 2.5 to 25% by weight of a polydimethylsiloxane-oil-based adhesive polymer composition, c) from 5 to 25% by weight of an absorption promoter, and d) from 25 to 95% by weight of volatile silicone solvent, said liquid solution being free of water, whereby, after evaporation of said volatile silicone solvent, a polydimethylsiloxane-oil-based film forms on the skin, which film transdermally delivers said lipophilic active ingredient to the patient.

2. Process as claimed in claim 1, in which the polydimethylsiloxane oils are selected from dimethicones of formula:

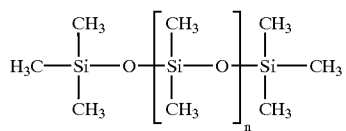

where n is an integer below 5000, and dimethiconols.

3. Process as claimed in claim 1, in which the adhesive polymer composition represents 2.5 to 12% of the weight of the solution.

4. Process as claimed in claim 1, in which the adhesive polymer composition represents 2.5 to 10% of the weight of the solution.

5. Process as claimed in claim 1, comprising 50 to 95% by weight of volatile silicones.

6. Process as claimed in claim 1, in which the volatile silicone is selected from the group consisting of polydimethylcyclosiloxanes and polysiloxanes of low molecular weight.

7. Process according to claim 1, said solution further comprising 0 to 25% by weight of a volatile solvent other than a volatile silicone.

8. Process as claimed in claim 1, in which the lipophilic active ingredient is selected from the group consisting of vitamin $D_3$ and its hydroxylated derivatives.

9. Process as claimed in claim 1, in which a defined dose of said solution is delivered on the skin and said dose is spread on the skin.

10. Process as claimed in claim 1, said liquid solution comprising:
   a) the lipophilic active ingredient selected from the group consisting of oestrogens, progestogens and mixtures thereof,
   b) from 2.5 to 25% by weight of the polydimethylsiloxane oil-based adhesive polymer composition,
   c) from 5 to 25% by weight of the absorption promoter, and
   d) from 35 to 55% by weight of the volatile silicone, and
   e) from 0 to 35% by weight of the volatile polar solvent.

11. Composition for transdermally administering a lipophilic active ingredient, said composition being a liquid solution comprising:
   a) a lipophilic active ingredient selected from the group consisting of hormones, steroids, and lipophilic vitamins,
   b) from 2.5 to 25% by weight of a polydimethylsiloxane-oil-based adhesive polymer composition,
   c) from 5 to 25% by weight of an absorption promoter, and
   d) from 35 to 95% by weight of volatile silicone solvent,
   said liquid solution being free from water and said solution forms, upon applying to the skin of a patient and evaporation of said volatile silicone solvent, a polydimethylsiloxane-oil-based film transdermally delivering said lipophilic active ingredient to the patient.

12. Composition as claimed in claim 11, for the formation of a film on the skin for the transdermal administration of a lipophilic active ingredient selected from the group consisting of oestrogens, progestogens, and mixtures thereof, said composition being a liquid solution which comprises:
   a) the lipophilic active ingredient, selected from oestrogens, progestogens and mixtures thereof,
   b) from 2.5 to 25% by weight of the polydimethylsiloxane-oil-based adhesive polymer composition,
   c) from 5 to 25% by weight of the absorption promoter,
   d) from 35 to 55% by weight of the volatile silicone solvent, and
   e) from 0 to 35% by weight of a volatile polar solvent,
   said liquid solution being free from water.

13. Composition for transdermally administering a lipophilic active ingredient, said composition being a liquid solution consisting essentially of:
   a) a lipophilic active ingredient selected from the group consisting of hormones, steroids, and lipophilic vitamins,
   b) from 2.5 to 25% by weight of a polydimethylsiloxane-oil-based adhesive polymer composition,
   c) from 5 to 25% by weight of an absorption promoter, and
   d) from 35 to 95% by weight of volatile silicone solvent,
   said liquid solution being free from water and said solution forms, upon applying to the skin of a patient and evaporation of said volatile silicone solvent, a polydimethylsiloxane-oil-based film transdermally delivering said lipophilic active ingredient to the patient.

* * * * *